Figure 3:
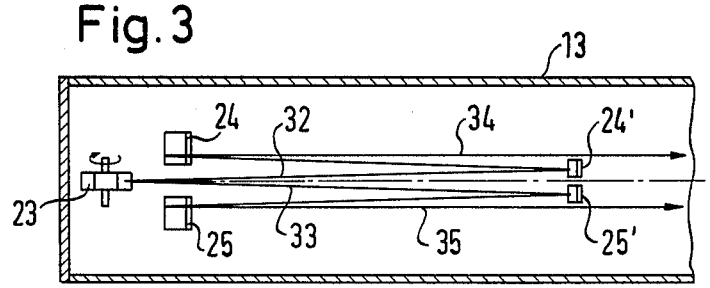

United States Patent [19]

Sick et al.

[11] 4,431,309

[45] Feb. 14, 1984

[54] MONITORING APPARATUS

[75] Inventors: Erwin Sick, Icking; Dieter Röss, Planegg; Siegfried Mankel, Geretsried, all of Fed. Rep. of Germany

[73] Assignee: Erwin Sick GmbH/Optik-Elektronik, Fed. Rep. of Germany

[21] Appl. No.: 223,067

[22] Filed: Jan. 7, 1981

[30] Foreign Application Priority Data

Jul. 7, 1980 [DE] Fed. Rep. of Germany ......... 300352

[51] Int. Cl.$^3$ .............................................. G01D 21/04
[52] U.S. Cl. ..................................... 356/431; 250/572
[58] Field of Search ...................... 356/429, 430, 431; 250/559, 562, 563, 571, 572

[56] References Cited

U.S. PATENT DOCUMENTS

| 2,547,623 | 4/1951 | Cockrell | 356/431 |
|---|---|---|---|
| 3,760,184 | 9/1973 | Brose | 356/430 |
| 4,004,152 | 1/1977 | Obser et al. | 356/431 |
| 4,013,367 | 3/1977 | Nagao et al. | 250/572 |
| 4,038,554 | 7/1977 | Craig | 356/431 |
| 4,040,745 | 8/1977 | Belleson et al. | 356/431 |
| 4,108,533 | 8/1978 | Sick et al. | 356/429 |
| 4,110,047 | 8/1978 | Takahashi | 356/430 |
| 4,116,527 | 9/1978 | Sick | 356/431 |
| 4,127,771 | 11/1978 | Sick | 350/6.6 |
| 4,260,899 | 4/1981 | Baker | 356/431 |
| 4,302,105 | 11/1981 | Sick | 250/572 |
| 4,310,250 | 1/1982 | Sick et al. | 356/431 |

FOREIGN PATENT DOCUMENTS

| 6601847 | 4/1969 | Fed. Rep. of Germany . |
| 2508366 | 9/1976 | Fed. Rep. of Germany . |
| 2602970 | 7/1977 | Fed. Rep. of Germany . |
| 2628543 | 8/1977 | Fed. Rep. of Germany . |
| 2727926 | 1/1979 | Fed. Rep. of Germany . |

OTHER PUBLICATIONS

Blaser et al., "Anwendungsergebnisse fotoelektronischer Verfahren zur Abtastung von Oberflächen, Abmessungen und Kennungen bei Förderung und Fertigung", *Automatik*, (Jan. 1971), pp. 6–13.

*Primary Examiner*—R. A. Rosenberger
*Attorney, Agent, or Firm*—Townsend & Townsend

[57] ABSTRACT

A light beam 2 from a laser light source 30 is split by a beam splitting arrangement 21, 22 into two slightly convergent light beams which are deflected by a deflecting mirror 31 onto the surface of a mirror wheel 23. The mirror wheel 23 that deflects these light beams via deflecting mirrors 24', 25' onto two strip-like concave mirrors 24, 25 which produce respective parallel scanning light beams which are continuously displaced parallel to themselves in the image spaces of the strip-like concave mirrors. These scanning light beams fall on respective rows of inclined dividing mirrors 9 and 10 which are arranged one behind the other in an alternating sequence. The inclined mirrors deflect the incident light beams through substantially 90° to form a continuous light curtain which can be used to scan web material. Light reflected from the surface of the web or transmitted through holes in the web falls on light gathering devices in the form of either two rows of strip-like Fresnel lenses 5, 6 or two rows of light conducting rods 5', 6'. One light gathering device is associated with each of the inclined mirrors 9, 10. Light gathered by each of the light gathering devices is directed to an associated photoelectric detector 7 which is connected to an electronic processing circuit 8 for evaluating the signals from all the photoelectric detectors.

7 Claims, 7 Drawing Figures

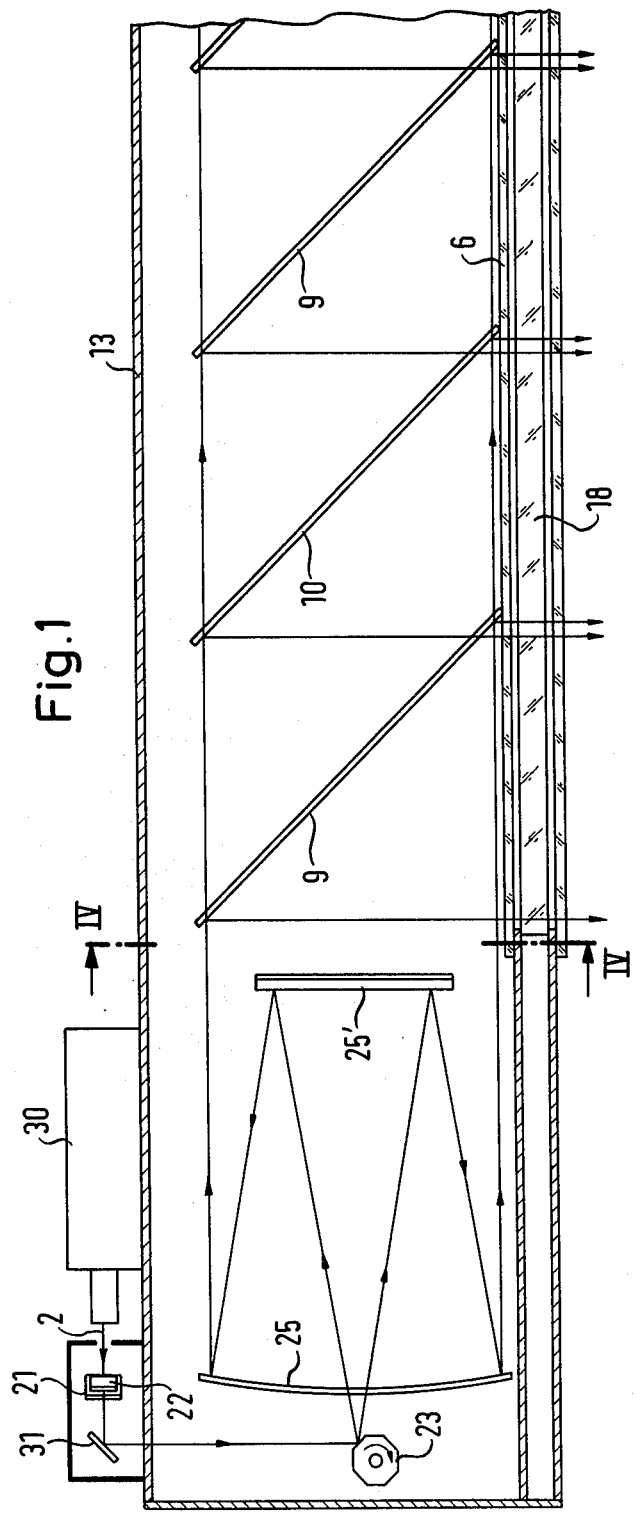
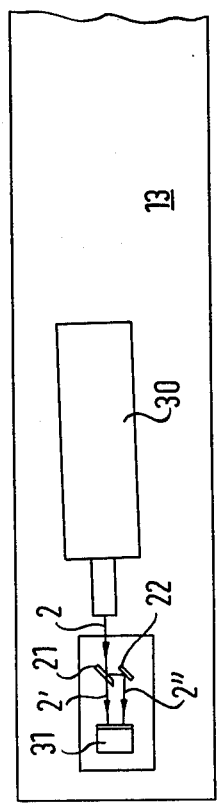

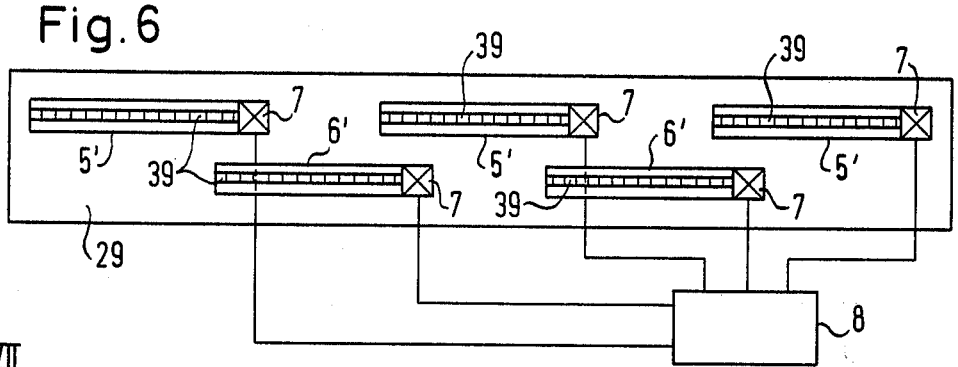
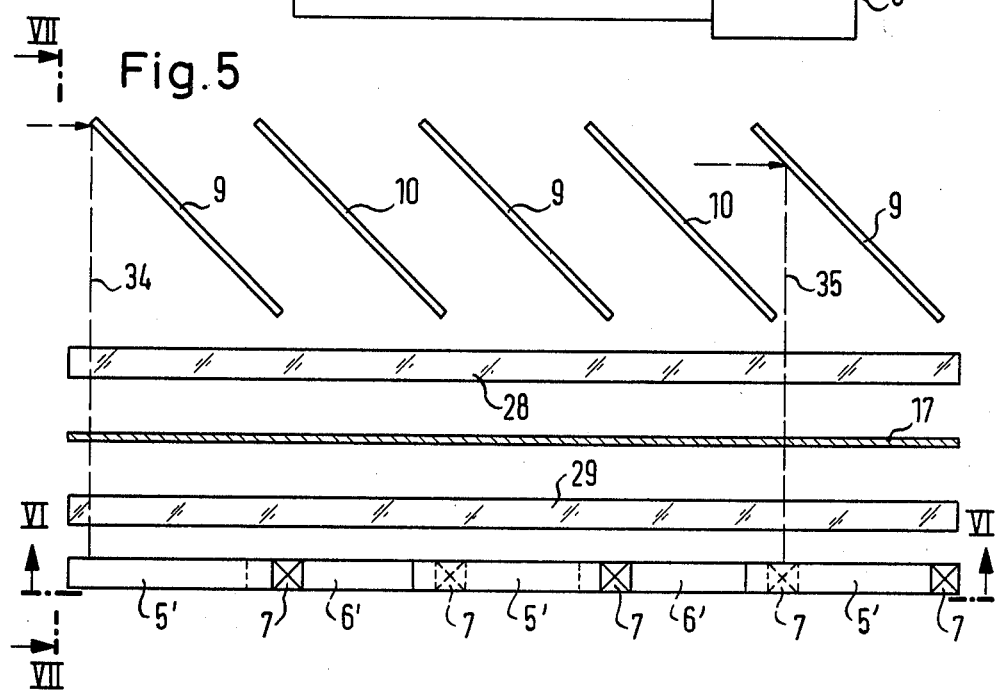
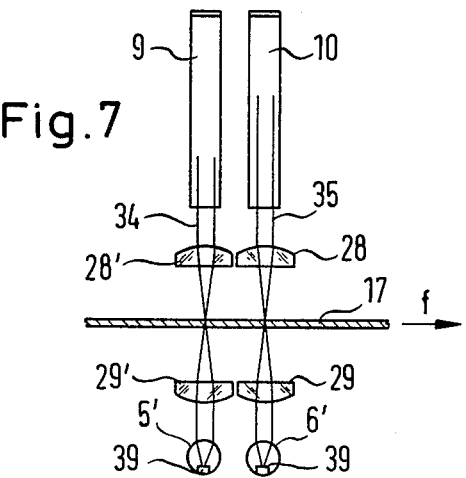

MONITORING APPARATUS

The present invention relates to monitoring apparatus and has particular reference to combined optical and electronic monitoring apparatus for detecting holes or surface defects in webs or other light reflecting surfaces.

A wide variety of apparatus is avaliable for monitoring webs or other light reflecting surfaces to establish the presence of defects. The known devices are however generally bulky and unnecessarily complicated and costly to manufacture.

The principal object underlying the present invention is to provide monitoring apparatus which is particularly compact and which can be readily manufactured. It is a further object of the present invention to provide an improved apparatus for detecting light remitted from the surface of a moving web of material.

To satisfy these objects the present invention envisages monitoring apparatus, in particular for monitoring for holes or surface defects in webs or other light reflecting surfaces, the apparatus comprising a light transmitting device including a laser light source for projecting a light curtain towards a surface under investigation; light receiving means for receiving light from said light curtain, after said light curtain has fallen on said surface, and for directing this light to photoelectric detection means and an electronic processing circuit for evaluating signals from said photoelectric detection means to signify the presence and/or nature of a defect in said surface; said light transmitting device comprising a plurality of inclined strip-like dividing mirrors arranged one behind the other in first and second rows in an alternating sequence, with the end regions of adjacent dividing mirrors of the sequence overlapping in the direction of the rows, and means for scanning light from said laser light source to form first and second scanning light beams which are incident on respective ones of said rows in the directions of these rows and which are deflected through substantially 90° by said dividing mirrors to form said light curtain; said light receiving means comprising a plurality of light gathering devices associated one with each of said dividing mirrors and arranged in first and second rows parallel to said first and second rows of dividing mirrors to either side of a central plane of symmetry of the apparatus and wherein said photoelectric detection means comprises at least one photoelectric detector in respect of each light gathering device.

This arrangement is particularly compact because all the components can be located in a common housing on one side of the web. The use of a plurality of inclined strip-like dividing mirrors arranged one behind the other in first and second rows in alternating sequence with the end regions of adjacent dividing mirrors of the sequence overlapping in the direction of the rows enables a very broad light curtain to be generated without gaps. Furthermore, the depths of the housing containing the monitoring apparatus can be kept relatively small for a given width of the scanning light curtain simply by increasing the number of strip-like dividing mirrors. The light gathering devices can readily be arranged closely adjacent the first and second rows of dividing mirrors so that the overall width of the housing can also be kept relatively small.

It is particularly advantageous if a cylindrical lens common to both the first and second rows of dividing mirrors and the first and second rows of light gathering devices extends between said rows and said surface under investigation with the focal line of said cylindrical lens lying on said surface.

A single cylindrical lens is thus advantageously used for both the light beams transmitted towards the surface under investigation from the first and second rows of strip-like dividing mirrors and for the light remitted from the surface under investigation to the light gathering devices.

The monitoring apparatus can also be used with advantage in an arrangement in which the surface under investigation takes the form of a web guided over the surface of a drum of which the axis of which lies parallel to the rows of dividing mirrors and light gathering devices and in the plane of symmetry of the apparatus. The radius of the drum should preferably be chosen so that the transmitted light beams following reflection the angular of specular reflection on the surface of the drum impinge centrally on the associated light gathering devices. In this way it is possible to ensure that specular reflection occurs into both the first and second rows of light gathering device which are spaced apart to either side of the central plane of symmetry.

An especially preferred light transmitter, which is compactly arranged and of simple construction, features an arrangement in which a light beam from said laser light source is split into first and second light beams via a beam divider and a deflecting mirror arranged parallel thereto with said first and second light beams converging on a mirror wheel arranged symmetrically at the focal point of two strip-like concave mirrors which are aligned with said first and second rows dividing mirrors whereby said first and second scanning light beams are generated in the image space of said strip-like concave mirrors.

In a further preferred embodiment the individual dividing mirrors of the first and second rows are transversely spaced apart from one another. This arrangement brings particular constructional advantages without disadvantageously affecting the optical quality of the apparatus. The transverse spacing between the individual mirrors advantageously amounts to approximately twice their width.

A particular preferred embodiment which is primarily intended for monitoring for holes makes use of light gathering devices in the form of first and second rows of light conducting rods which replace the strip-like Fresnel lenses and which each carry a photoelectric converter at at least one end face. All the photoelectric converters are once again preferably connected to a common electronic processing circuit.

In contrast to all known scanning devices using a light conducting rod the present invention makes use of numerous small light conducting rods which are arranged in first and second rows and displaced in the longitudinal direction in order to obtain a continuous scanning range without gaps. The light conducting rods preferably overlap in the longitudinal direction by an amount in the range from 2 to 30% and particularly by 15% of their lengths. I.e. the amount of overlap of one light conducting rod on the next adjacent conducting rod lies in the aforementioned range.

A common cylindrical lens can once again be associated with all the light conducting rods whereby the constructional complexity can be significantly reduced without disadvantageously reducing the optical quality of the apparatus.

The light gathering devices of the first and second rows can likewise be transversely spaced apart by an amount which preferably corresponds to their widths so that the mounting of the individual devices and their connection to the electronic processing circuit is possible in a straightforward manner.

Figure 4:
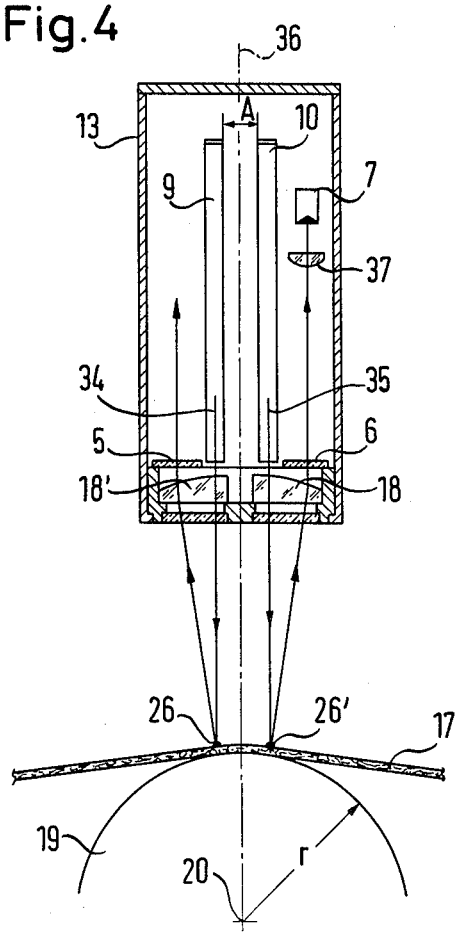

The invention will now be described in more detail and by way of example only with reference to the accompanying drawings which show:

FIG. 1 a partially sectioned schematic side view of a light transmitting device incorporated in a monitoring apparatus in accordance with the present invention, FIG. 2 a partially sectioned plan view of the device of FIG. 1 in the region of the laser light source, FIG. 3 a partially sectioned plan view of the device of FIG. 1 in the region of the mirror wheel, FIG. 4 a sectional view on the line IV—IV of FIG. 1, FIG. 5 a schematic side view of an embodiment of the monitoring apparatus of the present invention using small overlapping light conducting rods for the light gathering devices, FIG. 6 a view on the line VI—VI of FIG. 5 and FIG. 7 an end view of the arrangement of FIG. 5 as seen in the direction of the line VII—VII.

As seen in FIG. 1 a laser light source 30 is arranged above a housing 13 parallel to the direction of scanning. The laser light source directs a sharply defined light beam 2 to a partially transmitting mirror or beam divider 21 which is also illustrated in FIG. 2. The beam divider 21 splits the light beam 2 into first and second light beams 2', 2" with intensities in the ratio 1:1. For this purpose the second light beam 2" which is deflected at the surface of the beam divider 21 is once again deflected by a plane deflecting mirror 22 into the same direction as the first light beam 2" which is transmitted by the beam divider 21. The plane mirror 22 is so arranged that the first and second light beams 2', 2" converge slightly on one another so that they meet on the surface of a mirror wheel 23 after further deflection at a further plane deflecting mirror 31.

As shown in FIGS. 1 and 3 the mirror wheel generates first and second slightly divergent scanning light beams 32, 33 which impinge parallel to the direction of the laser 30 on two strip-like plane mirrors 24', 25' which are spaced apart sideways from each other. The first and second light beams 2', 2" extend at right angles to the scanning direction of the apparatus between the deflecting mirror 31 and the mirror wheel 23.

As seen in FIGS. 1 and 3 the strip-like plane mirrors 24', 25' reflect the incident scanning light beams 32, 33 to strip-like concave mirrors 24, 25. The optical arrangement is such that the mirror wheel sits at the focal point of these two concave mirrors. In this manner first and second scanning light beams 34, 35 emerge from the two concave mirrors 24, 25 with these light beams executing a parallel scanning movement in which they are continuously displaced parallel to themselves through the image spaces of their respective concave mirrors. These scanning light beams fall on respective first and second rows of strip-like dividing mirrors which are inclined at 45° to the incident scanning light beams. The dividing mirrors 9 and 10 are arranged one behind the other in first and second rows in an alternating sequence with the end regions of adjacent dividing mirrors of the sequence overlapping in the direction of the rows. Thus the scanning light beam 34 passes through all the mirrors 9 of the first row whereas the scanning light beam 35 passes through all the dividing mirrors of the second row 10. The reflectivity of the dividing mirrors of each of the rows progressively increases in accordance with a simple mathematical progression along the row so that the same fraction of the light beam is reflected into the light curtain region by each successive dividing mirror of the row. It will be appreciated that the last mirror of each row can be a fully reflecting mirror instead of a dividing mirror. The inclined dividing mirrors thus reflect the incident scanning light beams through substantially 90° and form a series of overlapping light curtains which can be used to scan across the full width of a web.

As seen in FIG. 4 the downwardly deflected scanning light beams 34, 35 impinge on a cylindrical lens 18 which extends over the whole length of the first and second rows of inclined mirrors. The cylindrical lens 18 projects the scanning light beams which form the light curtain to two adjacent positions 26, 26' on the surface of a material web 17 which is under investigation. This material web is tensioned over the surface of a drum 19 which is rotatable about an axis 20 which extends parallel to the first and second rows of inclined mirrors 9, 10 and lies in the central plane of symmetry 36 of the apparatus.

The scanning positions 26, 26' are spaced from the cylindrical lens 18 by a distance equivalent to its focal length.

As can be seen from FIG. 4 the inclined mirror strips 9, 10 are transversely spaced apart from each other in the first and second rows by a distance A which is approximately twice as large as their widths. The cylindrical lens 18 is arranged symmetrically to the vertical central plane 36 between the two rows of inclined mirror strips 9, 10.

As seen in the drawing the cylindrical lens extends on both sides significantly beyond the scanning light beams of the light curtain so that the outer regions of the cylindrical lens can be used for the reception of light reflected or remitted from the surface of the web 17. In order to receive this light strip-like Fresnel lenses which are displaced in their longitudinal directions are arranged in two rows above the outer regions of the cylindrical lens 18. These Fresnel lenses cooperate with the cylindrical lens 18 and further cylindrical lenses 37 to concentrate the received light on photoelectric detectors 7 which are associated one with each of the Fresnel lenses. In order to simplify the illustration a single photoelectric detector or converter 7 and a single cylindrical lens 37 are only shown on one side of the central plane of symmetry 36. A similar arrangement of photoconductors 7 and cylindrical lenses 37 displaced in the longitudinal direction of the rows of Fresnel lenses will be understood to be present on the other side of the central plane of symmetry 36.

As seen in FIG. 4 the radius r of the drum 19 is so chosen that the light beams falling onto the surface of the web 17 at the points 26, 26' pass through the outer regions of the cylindrical lens 18 and are deflected into the Fresnel lenses 5, 6 when specular reflection occurs at the surface of the web 17. This arrangement is thus particularly suitable for investigating metal surfaces to detect the presence of surface defects. The compact nature of the arrangement can be readily appreciated by having regard to FIG. 4 from which can be seen that the first and second rows of Fresnel lenses and the associated photoelectric detectors 7 can be arranged closely alongside the first and second rows of dividing mirrors 9, 10. To achieve as compact arrangement is is merely necessary to pay careful attention to the optical geometry of the apparatus.

FIG. 5 shows an analogous arrangement in which the Fresnel lenses are replaced by small light conducting rods 5', 6' with the light conducting rods being displaced in the longitudinal direction and arranged in first and second rows in an alternating sequence. This alternating sequence can be best seen by reference to FIG. 6. The arrangement is here however used not to determine faults in the surface of a web which manifest themselves by reflection but rather to detect holes in the surface of the web which manifest themselves in transmission. In this arrangement the light receiving device is arranged on the opposite side of the web from the light transmitting device. As seen in FIGS. 5 to 7 cylindrical lenses 28, 28', 29, 29' are provided both in front of the material web and behind the material web with these cylindrical lenses extending over the full lengths of the respectively associated first and second rows of light conducting rods and strip-like dividing mirrors. By way of example the cylindrical lens 28 concentrates the light curtain from the row of inclined mirrors 10 onto the surface of the web 17 and light passing through holes in the web falls on the second cylindrical lens 29 which then concentrates this light in the interior of the light conducting rods 6'. The second pair of cylindrical lenses 28', 29' function in the same manner. The light conducting rods themselves each have in known manner a stepped mirror arrangement 39 arranged along their surface facing the light entry surface. The individual mirrors of the stepped mirror arrangement serve to direct all incident light at angles of total reflection into the interior of the rod so that this light reaches a photoelectric detector 7 arranged at at least one end face of the light conducting rod. As seen in FIG. 6 all the photoelectric converters 7 are connected to a common electronic processing circuit 8.

As a result of the arrangement in accordance with the invention all the light conducting rods 5', 6' lying within one row are simultaneously able to receive light from the light curtain. The different signal received from the individual light conducting rods can be evaluated in the electronic processing circuit 8 and can be used to provide an indication of the location of the fault in the web. The present embodiment uses five light conducting rods spaced apart across the web so that five different detectors are connected to the electronic processing circuit.

The arrangements shown above make it possible to monitor a web 17 in the transverse direction totally without gaps. The direction of movement of the web is illustrated by the arrow f of FIG. 7.

It will finally be appreciated that the arrangement of FIGS. 5 to 7 could equally be operated using individual Fresnel lenses in place of the individual light conducting rods and that similarly the arrangement of FIGS. 1 to 4 could use light conducting rods in place of Fresnel lenses.

We claim:

1. Compact monitoring apparatus, in particular for monitoring for holes or surface defects in webs or the like, the apparatus comprising a light transmitting device including a laser light source for projecting a light curtain towards a surface under investigation; light receiving means for receiving light reflected from said surface and for directing the received light to photoelectric detection means; a housing having a central plane of symmetry, said housing containing said light transmitting device and said light receiving means; and an electronic processing circuit for evaluating signals from said photoelectric detection means to signify the presence and/or nature of a defect in said surface; said light transmitting device comprising a plurality of inclined strip-like dividing mirrors arranged one behind the other in first and second rows in an alternating sequence, wherein the end regions of adjacent dividing mirrors of the sequence overlap in the direction of the rows and said first and second rows are disposed on respective sides of said central plane of symmetry, and means for scanning light from said laser light source to form first and second scanning light beams which are incident on respective ones of said rows in the directions of these rows and which are deflected through substantially 90° by said dividing mirrors to form said light curtain; said light receiving means comprising a plurality of light gathering devices associated one with each of said dividing mirrors and arranged in first and second rows parallel to said first and second rows of dividing mirrors on either side of said central plane of symmetry of the apparatus wherein the light gathering devices are positioned closely adjacent the associated dividing mirrors, said light gathering devices and said dividing mirrors are located within said housing, said photoelectric detection means comprises at least one photoelectric detector in respect of each light gathering device; wherein cylindrical lens means are positioned in said light curtain with first portions on either side of said central plane of symmetry to direct said light curtain onto said surface and with second portions extending to either side of said central plane of symmetry beyond said dividing mirrors to direct light reflected from said surface to said light gathering devices, the apparatus further comprising a guide drum for guiding a web or the like under investigation past said housing, said guide drum having an axis lying parallel to said rows and lying in said central plane of symmetry and having a predetermined radius such that light passing through said first portions of said cylindrical lens means, impinging upon the surface of said web or the like under investigation at said guide drum, and being specularly reflected thereby will impinge upon said second portions of said cylindrical lens means to be directed to said light gathering devices.

2. Monitoring apparatus in accordance with claim 1 and wherein said cylindrical lens means comprises a single cylindrical lens common to both the first and second rows of dividing mirrors and the first and second rows of light gathering devices.

3. Monitoring apparatus in accordance with claim 1 and wherein a light beam from said laser light source is split into first and second light beams via a beam divider and a deflecting mirror arranged paralle thereto, with said first and second light beams converging on a mirror wheel arranged symmetrically at the focal point of two strip-like concave mirrors which are aligned with said first and second rows of dividing mirrors whereby said first and second scanning light beams are generated in the image space of said strip-like concave mirrors.

4. Monitoring apparatus in accordance with claim 1 and wherein the strip-like dividing mirrors in said first and second rows are transversely spaced apart from each other.

5. Monitoring apparatus in accordance with claim 4 and wherein the transverse spacing between the strip-like dividing mirrors amounts to approximately twice the width of said mirror.

6. Monitoring apparatus in accordance with claim 1 and wherein the light gathering devices are transversely spaced apart by an amount corresponding to their widths.

7. Monitoring apparatus in accordance with claim 1 and wherein the light gathering devices comprise Fresnel lenses.

* * * * *